United States Patent [19]
Beller et al.

[11] Patent Number: 5,831,107
[45] Date of Patent: Nov. 3, 1998

[54] PALLADACYCLES AND A PROCESS FOR THEIR PREPARATION

[75] Inventors: Matthias Beller, Garching; Hartmut Fischer, Hofheim; Wolfgang Anton Herrmann, Freising; Christoph Brossmer, Frankfurt, all of Germany

[73] Assignee: Aventis Research & Technology Deutschland, Germany

[21] Appl. No.: 762,971

[22] Filed: Dec. 10, 1996

Related U.S. Application Data

[63] Continuation-in-part of Ser. No. 493,147, Jun. 21, 1995, abandoned.

[30] Foreign Application Priority Data

Jun. 22, 1994 [DE] Germany .......................... 44 21 753.6

[51] Int. Cl.⁶ ........................ C07F 19/00; C07F 15/00; C07F 9/02
[52] U.S. Cl. ................ 556/16; 556/21; 556/22; 556/23; 556/136; 502/155; 502/162
[58] Field of Search ................... 556/21, 22, 23, 556/16, 136; 502/155, 162

[56] References Cited

PUBLICATIONS

Journal of the Chemical Society, *Transition Metal–Carbon Bonds. Part XXXIII. Internal Metallations of Secondary and Tertiary Carbon Atoms by Platinum (II) and Palladium (II)*, pp. 270–278 (1973).
Journal of Chemical Society, *Transition Metal–Carbon Bonds. Part XXXI. Internal Metallations of Palladium (II)–T–Butyldi–O–Tolylphosphine and –Di–T–Butyl–O–Tolylphosphine Complexes*, pp. 860–865, (1972).
Journal of the Chemical Society, Chemical Communications, 1972, *Internal Metallation of Tertiary and Secondary Carbon Atoms*, pp. 65–66, (1972).
Chemical Abstracts, vol. 110, No. 21, May 22, 1989, Abstract No. 193095f, *Crystal and Molecular Structures of Bis(Mu–Chloro) Bis (O–(Dimes Itylphosphino)–3,5–Dimethylbenzyl)Dipalladium(II) Acetone Solvate, Etc.*
Alyea, Elmer C., and Malito, John "Cyclometallation of Trimesitylphosphine", Journal of Organometallic Chemistry, 340 pp. 119–126 (1988).
Chemical Abstracts vol. 101, No. 12, Abstract No. 101670c (1984).
Synthesis, Nr. 3, *Cyclopalladated Complexes in Organic Synthesis*, pp. 233–252 (1985).
Chemical Abstracts vol. 125, Abstract No. 221376 (1996).
Chemical Abstracts vol. 124, Abstract No. 202611 (1996).
Chemical Abstracts vol. 124, Abstract No. 86116 (1996).

*Primary Examiner*—Porfirio Nazario-Gonzalez
*Attorney, Agent, or Firm*—Connolly & Hutz

[57] ABSTRACT

A palladacycle of the formula (I)

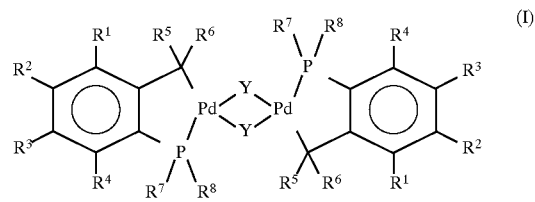

where:
  $R^1$, $R^2$, $R^3$, $R^4$, $R^5$ and $R^6$ are, independently of one another, hydrogen, $(C_1-C_4)$-alkyl, $(C_1-C_4)$-alkoxy, fluorine, $NH_2$, NH-alkyl$(C_1-C_4)$, N(alkyl)$_2$-$(C_1-C_4)$, $CO_2$-$(C_1-C_4)$alkyl, OCO-alkyl-$(C_1-C_4)$, or phenyl,
  $R^7$ and $R^8$ are, independently of one another, $(C_1-C_8)$-alkyl, $(C_3-C_{12})$-cyloalkyl, substituted or unsubstituted aryl
  or where $R^1$, and $R^2$, $R^2$ and $R^3$, $R^3$ and $R^4$, $R^5$ and $R^6$ together form an aliphatic or aromatic ring, and
  Y is an anion of an inorganic or organic acid.

20 Claims, No Drawings

PALLADACYCLES AND A PROCESS FOR THEIR PREPARATION

RELATED APPLICATIONS

This application is a continuation-in-part of U.S. Ser. No 08/493,147, filed Jun. 21, 1995 now abandoned.

DESCRIPTION OF THE PRIOR ART

The invention relates to novel palladacycles and a process for their preparation.

U.S. Ser. No. 08/493,359 filed Jun. 21, 1995, which is incorporated by reference in its entirety describes a new advantageous process using this type of catalyst.

Palladacycles play an important role as catalysts for a series of processes. Examples of such processes which may be mentioned are the synthesis of substituted styrenes, the preparation of stilbenes and cinnamic acids from aryl halides.

The literature describes
trans-di-$\mu$-bromo-bis[o-(ditolylphosphino)benzyl]-dipalladium(II) (R. F. Heck et al., J. Org. Chem. 49, (1984) 1940)
trans-di-$\mu$-chloro-bis[o-(ditolylphosphino)benzyl]-dipalladium(II)
trans-di-$\mu$-iodo-bis[o-(ditolylphosphino)benzyl]dipalladium (II)
trans-di-$\mu$-bromo-bis[o-(dimesitylphosphino)-3,5-dimethylbenzyl]dipalladium (II) (E. C. Algea, J. Malito, J. Organomet. Chem. 340 (1988) 199)
trans-di-$\mu$-chloro-bis[o-(dimesitylphosphino)-3,5-dimethylbenzyl]dipalladium (II)
trans-di-$\mu$-iodo-bis[o-(dimesitylphosphino)-3,5-dimethylbenzyl]dipalladium(II)
trans-di-$\mu$-acetato-bis[o-(t-butyl-o-tolylphosphino)benzyl] dipalladium (II) (G. Y. Gainsford, R. Mason, J. Organomet. Chem. 80 (1974) 395)
trans-di-$\mu$-acetato-bis[o-(di-t-butylphosphino)benzyl]-palladium(II) (A. Y. Cheney, B. L. Shaw J. Chem. Soc. Dalton Trans. (1972) 860).

In view of the many possible uses of palladacycles, there is a need for new palladacycles, on the one hand to supplement and to extend the spectrum of their possible applications and, on the other hand, to be able to carry out certain reactions particularly favorably.

This object is achieved by palladacycles of the formula (I)

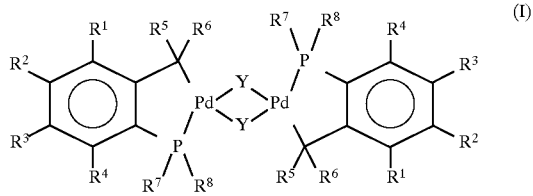

(I)

where:
$R^1$, $R^2$, $R^3$, $R^4$, $R^5$ and $R^6$ are, independently of one another, hydrogen, ($C_1$–$C_4$)-alkyl ($C_3$–$C_{12}$)-cycloalkyl, ($C_1$–$C_4$)-alkoxy, fluorine, $NH_2$, NH-alkyl($C_1$–$C_4$), N(alkyl)$_2$-($C_1$–$C_4$), $CO_2$-($C_1$–$C_4$)-alkyl, OCO-alkyl-($C_1$–$C_4$), or phenyl, $R^7$ and $R^8$ are independent of one another ($C_1$–$C_8$)-alkyl, ($C_3$–$C_{12}$)-cycloalkyl, substituted or unsubstituted aryl or where $R^1$ and $R^2$, $R^2$ and $R^3$, $R^3$ and $R^4$, $R^5$ and $R^6$ together form an aliphatic or aromatic ring, and Y is an anion of an inorganic or organic acid, with the exception of the compounds:

trans-di-$\mu$-bromo-bis{o-(ditolylphosphino)benzyl}dipalladium(II),
trans-di-$\mu$-iodo-bis{o-(ditolylphosphino)benzyl}dipalladium(II),
trans-di-$\mu$-bromo-bis{o-dimesitylphosphino)-3,5-dimethylbenzyl}dipalladium(II),
trans-di-$\mu$-chloro-bis{o-(dimesitylphosphino)-3,5-dimethylbenzyl}dipalladium(II),
trans-di-$\mu$-iodo-bis{o-(dimesitylphosphino)-3,5-dimethylbenzyl}dipalladium(II),
trans-di-$\mu$-acetato-bis{o-(t-butyl-o-tolylphosphino)benzyl}dipalladium(II),
trans-di-$\mu$-acetato-bis{o-di-t-butylphosphino)benzyl}dipalladium(II),
trans-di-$\mu$-chloro-bis-{o-(t-butyl-o-tolyphosphino)benzyl}dipalladium(II),
trans-di-$\mu$-chloro-bis{o-(di-t-butylphosphino)benzyl}dipalladium(II),
trans-di-$\mu$-benzato-bis{o-(t-butyl-o-tolyphosphino)benzyl}dipalladium(II),
trans-di-$\mu$-benzato-bis{o-(di-t-butylphosphino)benzyl}dipalladium(II) and
trans-di-$\mu$-chloro-bis{1-o(di-t-butylphosphino)phenyl)ethyl}dipalladium(II).

In a preferred embodiment the palladacycles are of the formula (I) where:
$R^1$, $R^2$, $R^3$, $R^4$, $R^5$ and $R^6$ are, independently of one another, hydrogen, ($C_1$–$C_4$)-alkyl ($C_3$–$C_{12}$)-cycloalkyl, ($C_1$–$C_4$)-alkoxy, fluorine, $NH_2$, NH-alkyl($C_1$–$C_4$), N(alkyl)$_2$-($C_1$–$C_4$), $CO_2$-($C_1$–$C_4$)-alkyl, OCO-alkyl-($C_1$–$C_4$), or phenyl, $R^7$ and $R^8$ are independent of one another ($C_1$–$C_8$)-alkyl, ($C_3$–$C_{12}$)-cycloalkyl, substituted or unsubstituted aryl or where $R^1$ and $R^2$, $R^2$ and $R^3$, $R^3$ and $R^4$, $R^5$ and $R^6$ together form an aliphatic or aromatic ring, and Y is an anion of an inorganic or organic acid, with the exception of the compounds:

trans-di-$\mu$-bromo-bis{o-(ditolylphosphino)benzyl}dipalladium(II),
trans-di-$\mu$-iodo-bis{o-(ditolylphosphino)benzyl}dipalladium(II),
trans-di-$\mu$-bromo-bis{o-dimesitylphosphino)-3,5-dimethylbenzyl}dipalladium(II),
trans-di-$\mu$-chloro-bis{o-(dimesitylphosphino)-3,5-dimethylbenzyl}dipalladium(II),
trans-di-$\mu$-iodo-bis{o-(dimesitylphosphino)-3,5-dimethylbenzyl}dipalladium(II),
trans-di-$\mu$-acetato-bis{o-(t-butyl-o-tolylphosphino)benzyl}dipalladium(II),
trans-di-$\mu$-acetato-bis{o-di-t-butylphosphino)benzyl}dipalladium(II),
trans-di-$\mu$-chloro-bis-{o-(t-butyl-o-tolyphosphino)benzyl}dipalladium(II),
trans-di-$\mu$-chloro-bis{o-(di-t-butylphosphino)benzyl}dipalladium(II),
trans-di-$\mu$-benzato-bis{o-(t-butyl-o-tolyphosphino)benzyl}dipalladium(II),
trans-di-$\mu$-benzato-bis{o-(di-t-butylphosphino)benzyl}dipalladium(II),
trans-di-$\mu$-chloro-bis{1-o(di-t-butylphosphino)phenyl)ethyl}dipalladium(II) and
trans-di-$\mu$-chloro-bis-{o-(ditolylphosphino)benzyl}dipalladium(II).

Palladacycles of interest are those of the formula (I) in which:
$R^1$, $R^2$, $R^3$ and $R^4$ independently of one another are hydrogen, ($C_1$–$C_4$)-alkyl, ($C_1$–$C_4$)-alkoxy, fluorine, phenyl, cycloalkyl-($C_5$–$C_8$), R[5] and R[6] independently of one another are hydrogen, ($C_1$–$C_4$)-alkyl, R[7] and R[8] independently of one another are ($C_1$–$C_8$)-alkyl, ($C_3$–$C_{12}$)-cycloalkyl, phenyl, tolyl, xylyl, mesityl, naphthyl or anthracenyl, which can be substituted by from 1 to 3 ($C_1$–$C_4$)-alkyl groups.

Important palladacycles are, inter alia, those of the formula (I) in which:

R[1], R[2], R[3] and R[4] independently of one another are hydrogen, ($C_1$–$C_4$)-alkyl or phenyl, R[5] and R[6] independently of one another are hydrogen or ($C_1$–$C_4$)-alkyl, R[7] and R[8] independently of one another are phenyl, o-tolyl, cyclohexyl, tert. amyl, isopropyl or tert. butyl.

Y is preferably acetate, cyanide, trifluoroacetate, tetrafluoroborate, propionate, benzoate, chloride, bromide, iodide, fluoride, sulfate, hydrogensulfate, nitrate, phosphate, hexafluorophosphate, tetrafluoroborate, tosylate, mesylate, acetylacetonate, hexafluoroacetylacetonate or pyrazolyl.

Of particular importance are, for example, trans-di-μ-acetato-bis[o-(di-o-tolylphosphino)benzyl]dipalladium(II)

trans-di-μ-chloro-bis[o-(di-o-tolylphosphino)benzyl]dipalladium(II)

trans-di-μ-acetato-bis[o-(dimesitylphosphino)-3,5-dimethylbenzyl]dipalladium (II)

di-μ-acetato-bis[o-(cyclohexyl-o-tolylphosphino)benzyl]dipalladium(II).

The palladacycles of the invention represent a new class of catalyst. The catalysis results in the olefination of aryl halides are exceptional in comparison with the prior art, so that there is great industrial interest in the catalysts of the invention.

The invention further provides a process for preparing compounds of formula (I) described above, which comprises reacting a phosphane of the formula (II)

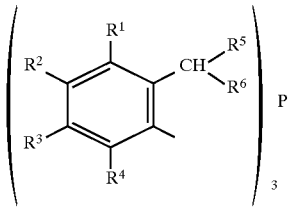

where R[1] to R[6] are as defined above, with a palladium salt of the formula (III), a palladium complex of the formula (IV) or an alkali metal palladate of the formula (V)

$$Pd\ Y_2(III)\quad Pd\ Y_2L_2(IV)\quad M_2[PdY_4]\quad (V)$$

where Y is as defined above, M is sodium, potassium or lithium and L is 1,5-cyclooctadiene, acetonitrile or benzonitrile, in the presence of an organic solvent.

In many cases it has been found to be useful to carry out the reaction at a temperature of from about 0° to about 160° C., in particular from about 10° to about 150° C., preferably from about 15° to about 140° C. It has also been found to be favorable to use the phosphane of the formula (II) and the palladium compound of the formula (III), (IV) or (V) in a molar ratio of from about 0.1 to about 20, in particular from about 0.15 to about 15, preferably from about 0.2 to about 10.

Suitable solvents are, for example, hydrocarbons such as but not limited to, mesitylen, methylnaphthaline, anisole, tert. butylmethylether, di-n-butylether, methanol, ethanol, propanol, butanol, acetic acid, acetic acid ester, polyethylene or aromatic hydrocarbons, such as toluene and xylene.

For the preparation of relatively sparingly soluble palladacycles, it is also possible to react a more readily soluble palladacycle with the corresponding anion of an organic or inorganic acid.

The examples are to illustrate the invention, without restricting it to them.

EXAMPLE 1 trans-Di-(μ-acetato-bis[o-(di-o-tolylphosphino)benzyl]dipalladium(II) (1)

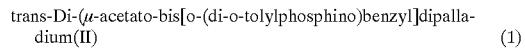

4.5 g (20 mmol) of Pd(Oac)$_2$ are dissolved in 500 ml of toluene, giving a reddish brown coloration. The solution is admixed with 8.0 g (26.3 mmol) of tri(o-tolyl)phosphane. The solution which rapidly becomes clear and light orange in colors is heated for 3 minutes at barely 50° C. and then cooled to room temperature. The solvent is removed in vacuo to ¼ of the volume. After addition of 500 ml of hexane, the precipitate formed is filtered off. This gives 8.8 g (93% of theory, based on Pd(Oac)$_2$) of (1) as a yellow solid (mp.>200° C.). (1) can be isolated in analytically pure form yellow crystalline needles by recrystallization from toluene/hexane or methylene chloride/hexane and filtration of the solutions through Celite®.

Elemental analysis: Found: C, 58.89%; H, 5.06%; P, 6.92%; 0, 6.47%; Pd, 21.84%; $C_{46}H_{46}O_4P_2Pd_2$ (937.62) Calc.: C, 58.93%; H, 4.94%; P, 6.61%; 0, 6.83%; Pd, 22.70%;

IR (cm$^{-1}$, KBr): 3052 m, 3007 m, 2954 w, 2925 m ν(CH); 1578 vs ν($μ_2$–C=0), 1468 s; 1630 ν(C=C); 1578, 1416 ν($μ_2$–C0) 1341;

$^1$H-NMR (400 Mhz, –70° C., CD$_2$Cl$_2$): δ=7.31 (4H, m, H$_{tolyl}$); 7.21 (2H, m, H$_{tolyl}$); 7.12 (6H, m, H$_{tolyl}$); 7.06(2H, t, H$_{benzyl}$, $^3$J(HH)=7.3 Hz); 6.92 (4H, m, H$_{tolyl}$);6.70 (2H, t, H$_{benzyl}$, $^3$J(HH)=7.3 Hz); 6.56 (2H, t, H$_{benzyl}$, $^3$J(HH)=9 Hz); 6.35 (2H, dd, H$_{benzyl}$, $^3$J(HH)=7.9 Hz, $^4$J(PH)=12.2 Hz); 3.00 (6H, s, CH$_3$); 2.81 (2H, dd, CH$_a$H$_b$, $^2$J(H$_a$H$_b$)=14.0 Hz, $^3$J(PH)=4.3 Hz); 2.40 (2H, dd, CH$_a$H$_b$, $^2$J(H$_a$H$_b$)=14.0 Hz, $^3$J(PH)=1.8 Hz); 2.10 (6H, s, CH$_3$); 1.91 (s, 6H, CR$_3$);

$^{13}$C{$^1$H}-NMR (100.5 Mhz, –70° C., CD$_2$Cl$_2$): δ=178.5 (s, CH$_3$CO$_2$); 157.1 (d, C$_{Ar}$, J(PC)=31.3 Hz); 141.1 (d, C$_{Ar}$, J(PC)=16.0 Hz); 141.0 (d, C$_{Ar}$, J(PC)=21.0 Hz); 133.0 (s, C$_{Ar}$); 132.5 (d, C$_{Ar}$, J(PC)=4.6 Hz); 132.4 (d, C$_{Ar}$, J(PC)=6.1 Hz); 131.7 (d, C$_{Ar}$, J(PC)=8.8 Hz); 131.4 (d, C$_{Ar}$, J(PC)=13.7); 131.3 (d, C$_{Ar}$, J(PC)=9.9 Hz); 130.4 (d, C$_{Ar}$, J(PC)=16.0 Hz); 129.9 (s, C$_{Ar}$); 129.1 (d, C$_{Ar}$, J(PC)=46.2 Hz); 128.7 (s, C$_{Ar}$); 128.1 (d, C$_{Ar}$, J(PC)=33.2 Hz); 127.6 (d, C$_{Ar}$, J(PC)=23.7 Hz); 125.6 (d, C$_{Ar}$, J(PC)=7.3 Hz); 125.2 (d, C$_{Ar}$, J(PC)=7.3 Hz); 124.9(d, C$_{Ar}$, J(PC)=11.4 Hz); 30.8 (s, CH$_2$); 24.7 (d, $\underline{C}$H$_3$C0$_2$, 4J(PC)=3.1 Hz); 23.0 (d, CH$_3$, 3J(PC)=13.7 Hz); 22.2 (d, CH$_3$, 3J(PC)=6.9 Hz);

$^{31}$P{$^1$H}-NMR (161.9 Mhz, –70° C., CD$_2$Cl$_2$): δ=34.2 (s); CI-MS(150 Ev): m/e=939 [M$^+$+H], 880 [M$^+$–Oac], 819 [M+–2Oac], 714 [Pd{o-CH$_2$C$_6$H$_4$P(o-tol)$_2$}$_2^+$].

EXAMPLE 2 trans-Di-μ-chloro-bis[o-(di-o-tolylphosphino)benzyl]dipalladium(II) (2)

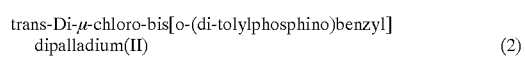

250 mg (0.27 mmol) of Pd$_2$(Oac)$_2${o-CH$_2$C$_6$H$_4$P(o-tol)$_2$}$_2$ are dissolved in 20 ml of methylene chloride, admixed with 1.00 g (3.38 mmol) of [NBu$_4$]Cl and stirred for 1 hour at room temperature. The solvent is removed in vacuo and the residue is taken up in 30 ml of methanol. The fine, yellow precipitate is filtered off, washed three times with 20 ml of methanol and twice with 20 ml of pentane and dried in vacuo. This gives 237 mg (100% of theory) of (2) as a yellow solid which is sparingly soluble in $CH_2Cl_2$ and DMF.

Elemental analysis Found: C, 56.29; H, 4.57; P, 7.04; Cl, 8.14; Pd, 23.49%. $C_{42}H_{40}{}_{Cl2}P_2Pd_2$(890.43) Calc.: C, 56.65; H, 4.53; P, 6.96; Cl, 7.96; Pd, 23.90%;

$^{31}P-\{^1H\}$-NMR ($CD_2Cl_2$ with additional of [$Nbu_4$]Cl, 20° C., 161.85 Mhz); δ=39.3 (s);

CI-MS (150 Ev):m/e=891 [M$^+$+H], 481 [Pd{o-$CH_2C_6H_4$P(o-tol)$_2$}$Cl_2{}^+$], 444 [Pd{o-$CH_2C_6H_4$P(o-tol)$_2$}Cl$^+$].

EXAMPLE 3 trans-Di-μ-acetato-bis[o-(dimesitylphosphino)-3,5-dimethylbenzyl] dipalladium(II) (3)

1.30 g (5.80 mmol) of palladium(II) acetate are dissolved in 200 ml of toluene giving a reddish brown coloration and admixed with 2.30 g (5.91 mmol) of trimesitylphosphane P(Mes)$_3$. The mixture is stirred for 12 hours at room temperature, with the color of the solution gradually changing to dark yellow. The toluene solution is subsequently filtered through a frit packed with Celite® or syringed through a Whatman® filter to remove traces of elemental palladium. After complete removal of the solvent in vacuo, the residue is taken up in from 10 to 20 ml of diethyl ether and stirred with slight cooling (ice bath) until (from 1 to 12 hours) a voluminous, yellow precipitate is formed. The precipitate is filtered off, washed with a little with cold diethyl ether and pentane (5 ml of each) and dried in vacuo. This gives 2.60 g (81% of theory) of (3) as a yellow solid which is soluble both in $Et_2O$ and in hexane. To obtain an analytically pure product, traces of free P(Mes)$_3$ have to be removed by chromatography (silica gel/50% $CH_2Cl_2$/n-hexane) Recrystallization of the complex leads to yield losses, since (3) and P(Mes)$_3$ have similar solubility properties.

$^{31}P-\{^1H\}$-NMR($CD_2Cl_{21}$–70° C., 161.85 Mhz): δ=25.6 (s); CI-MS (150 Ev):m/e=1106 [M$^+$], 1047 [M$^+$–Oac], 988 [M$^+$–2OAc), 881 [Pd{o-$CH_2C_6H_2(CH_3)_2$P(Mes)$_2$}$^+$].

EXAMPLE 4

Di-μ-acetato-bis[o-(cyclohexyl-o-tolylphosphino)benzyl]dipalladium(II) (4)

1.75 g (7.80 mmol) of Pd(Oac)$_2$ are dissolved in 200 ml of toluene, admixed with 2.45 g (8.27 mmol) of di(o-tolyl)cyclohexylphosphane and stirred for 6 hours at room temperature. The solvent is removed in vacuo and the residue is suspended in 30 ml of diethyl ether. The whitish precipitate which separates out is filtered off, dried and taken up in 20 ml of toluene. The solution or suspension thus obtained is filtered through a frit packed with Celite® to remove elemental palladium and sparingly soluble byproducts. The orange to light yellow colored filtrate is evaporated to dryness in vacuo and the residue is recrystallized at –30° C. from methylene chloride/n-hexane or toluene/n-hexane. This gives 1.5 g (42% of theory) of (4) in the form of pale yellow to colorless crystals.

Elemental analysis Found: C, 57.15%; H, 5.87%; P, 6.94%; 0, 6.84%; Pd, 23.02%; $C_{44}H_{54}O_4P_2Pd_2$ (921.66) Calc.: C, 57.34%; H, 5.91%; P 6.72%; 0, 6.94%; Pd, 23.09%;

$^1H$-NMR ($CD_2Cl_2$, 20° C., 400 Mhz): d=7.4–6.8 (16H, m, Haryl); 2.8–2.2 (4H, m, $CH_2$); 2.41 (3H, s, $CH_3$); 2.15 (3H, s, $CH_3$); 1.88 (6H, s, $CH_3$); 2.0–0.7 (22H, b, HCy);

$^{31}P-\{^1H\}$-NMR($CD_2Cl_2$, 20° C., 161.85 Mhz): δ=57.8 (s,trans-isomer), 56.0–55.0 (b, cis-isomer); ($CD_2Cl_2$, –90° C., 161.85 Mhz): δ=62 (m and b, trans-isomer, 54 (m and b, cis-isomer).

CI-MS (150 Ev): m/e=923 (M$^+$+H], 697 [Pd{o-$CH_2C_6H_4$P(o-tol) (Cy)}$_2{}^+$].

While there is shown and described herein certain specific structure embodying the invention, it will be manifest to those skilled in the art that various modifications and rearrangements of the parts maybe made without departing from the spirit and scope of the underlying inventive concept and that the same is not limited to the particular forms herein shown and described.

We claim:

1. A palladacycle of the formula (I)

(I)

where:
- R$^1$, R$^2$, R$^3$, R$^4$, R$^5$ and R$^6$ are, independently of one another, hydrogen, (C$_1$–C$_4$)-alkyl, (C$_1$–C$_4$)-alkoxy, fluorine, NH$_2$, NH-alkyl(C$_1$–C$_4$), N(alkyl)$_2$-(C$_1$–C$_4$), CO$_2$-(C$_1$–C$_4$)alkyl, OCO-alkyl-(C$_1$–C$_4$), or phenyl,
- R$^7$ and R$^8$ are, independently of one another, (C$_1$–C$_8$)-alkyl, (C$_3$–C$_{12}$)-cycloalkyl, substituted or unsubstituted aryl
- or where R$^1$ and R$^2$, R$^2$ and R$^3$, R$^3$ and R$^4$, R$^5$ and R$^6$ together form an aliphatic or aromatic ring, and
- Y is an anion of an inorganic or organic acid, with the exception of the compounds:

trans-di-μ-bromo-bis{o-(ditolylphosphino) benzyl}dipalladium(II), trans-di-μ-iodo-bis{o-(ditolylphosphino) benzyl}dipalladium(II), trans-di-μ-bromo-bis{o-dimesitylphosphino)-3,5-dimethylbenzyl}dipalladium(II), trans-di-μ-chloro-bis{o-(dimesitylphosphino)-3,5-dimethylbenzyl}dipalladium(II), trans-di-μ-iodo-bis{o-(dimesitylphosphino)-3,5-dimethylbenzyl}dipalladium(II), trans-di-μ-acetato-bis{o-(t-butyl-o-tolylphosphino) benzyl}dipalladium(II), trans-di-μ-acetato-bis{o-di-t-butylphosphino) benzyl}dipalladium(II), trans-di-μ-chloro-bis-{o-(t-butyl-o-tolyphosphino) benzyl}dipalladium(II), trans-di-μ-chloro-bis{o-(di-t-butylphosphino) benzyl}dipalladium(II), trans-di-μ-benzato-bis{o-(t-butyl-o-tolyphosphino) benzyl}dipalladium(II), trans-di-μ-benzato-bis{o-(di-t-butylphosphino) benzyl}dipalladium(II), trans-di-μ-chloro-bis{1-o(di-t-butylphosphino)phenyl) ethyl}dipalladium(II) and trans-di-μ-chloro-bis{o-(ditolylphosphino) benzyl}dipalladium(II).

2. The palladacycle as claimed in claim 1, wherein
R$^1$, R$^2$, R$^3$ and R$^4$, independently of one another, are hydrogen, (C$_1$–C$_4$)-alkyl, (C$_1$–C$_4$)-alkoxy, fluorine or phenyl, $R^5$ and $R^6$, independently of one another, are hydrogen or $(C_1-C_4)$-alkyl, $R^7$ and $R^8$, independently of one another, are $(C_1-C_8)$-alkyl, $(C_3-C_{12})$-cycloalkyl, phenyl, naphthyl or anthracenyl, which optionally are substituted by from 1 to 3 $(C_1-C_4)$-alkyl groups.

3. The palladacycle as claimed in claim 1, wherein $R^1$, $R^2$, $R^3$ and $R^4$, independently of one another, are hydrogen or $(C_1-C_4)$-alkyl, $R^5$ and $R^6$, independently of one another, are hydrogen or $(C_1-C_4)$-alkyl, $R^7$ and $R^8$, independently of one another, are phenyl, o-tolyl, cyclohexyl or butyl and Y is acetate, cyanide, trifluoroacetate, tetrafluoroborate, propionate, benzoate, chloride, bromide, iodide, fluoride, sulfate, hydrogensulfate, nitrate, phosphate, hexafluorophosphate, tetrafluoroborate, tosylate, mesylate, acetylacetonate, hexafluoroacetylacetonate or pyrazolyl.

4. The palladacycle as claimed in claim 1, wherein said palladacycle is selected from the group consisting of:

trans-di-$\mu$-acetato-bis{o-(di-o-tolylphosphino)benzyl}dipalladium(II), trans-di-$\mu$-acetato-bis{o-dimesitylphosphino)-3,5-dimethylbenzyl}dipalladium(II) and di-$\mu$-acetato-bis{o-(cyclohexyl-o-tolylphosphino)benzyl}dipalladium(II).

5. A process for preparing a sparingly soluble palladacycle which comprises reacting the palladacycle as claimed in claim 1 with an anion of an inorganic or organic acid to give the sparingly soluble palladacycle.

6. A process for preparing a palladacycle of the formula (I)

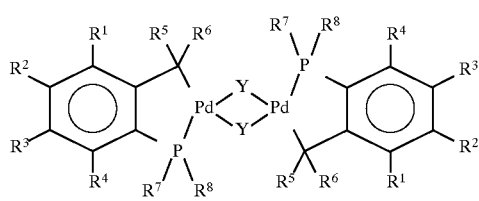

where:

$R^1$, $R^2$, $R^3$, $R^4$, $R^5$ and $R^6$ are, independently of one another, hydrogen, $(C_1-C_4)$-alkyl, $(C_1-C_4)$-alkoxy, fluorine, $NH_2$, NH-alkyl$(C_1-C_4)$, N(alkyl)$_2$-$(C_1-C_4)$, $CO_2$-$(C_1-C_4)$alkyl, OCO-alkyl-$(C_1-C_4)$, or phenyl, $R^7$ and $R^8$ are, independently of one another, $(C_1-C_8)$-alkyl, $(C_3-C_{12})$-cycloalkyl, substituted or unsubstituted aryl or where $R^1$ and $R^2$, $R^2$ and $R^3$, $R^3$ and $R^4$, $R^5$ and $R^6$ together form an aliphatic or aromatic ring, and Y is an anion of an inorganic or organic acid, which comprises reacting a phosphane of the formula (II)

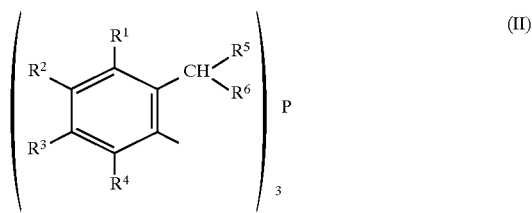

where $R^1$ to $R^6$ are as defined above with a palladium salt of the formula (III), a palladium complex of the formula (IV) or an alkali metal palladate of the formula (V)

$$Pd\ Y_2 \quad (III)$$

$$Pd\ Y_2L_2 \quad (IV)$$

$$M_2\{PdY_4\} \quad (V)$$

where Y is as defined above M is sodium, potassium or lithium and L is 1,5-cyclooctadiene, acetonitrile or benzonitrile, in the presence of a substituted aromatic hydrocarbon.

7. The process as claimed in claim 6, wherein the reaction is carried out at a temperature from 0° to 160° C.

8. The process as claimed in claim 6, wherein the phosphane of the formula (II) is used in a molar ratio to the palladium compound of the formula (III), (IV) or (V) of from 0.1 to 20.

9. The process as claimed in claim 8, wherein the reaction is carried out at a temperature from 10° to 150° C.

10. The process as claimed in claim 8, wherein the reaction is carried out at a temperature from 15° to 140° C.

11. The process as claimed in claim 9, wherein the phosphane of the formula (II) is used in a molar ratio to the palladium compound of the formula (III), (IV) or (V) of from 0.15 to 15.

12. The process as claimed in claim 10, wherein the phosphane of the formula (II) is used in a molar ratio to the palladium compound of the formula (III), (IV) or (V) of from 0.2 to 10.

13. The process as claimed in claim 8, wherein the solvents are toluene or xylene.

14. The process as claimed in claim 6, wherein $R^1$, $R^2$, $R^3$ and $R^4$, independently of one another, are hydrogen, $(C_1-C_4)$-alkyl, $(C_1-C_4)$-alkoxy, fluorine or phenyl, $R^5$ and $R^6$, independently of one another, are hydrogen or $(C_1-C_4)$-alkyl, $R^7$ and $R^8$, independently of one another, are $(C_1-C_8)$-alkyl, $(C_3-C_{12})$-cycloalkyl, phenyl, naphthyl or anthracenyl, which optionally are substituted by from 1 to 3 $(C_1-C_4)$-alkyl groups.

15. The process as claimed in claim 6, wherein $R^1$, $R^2$, $R^3$ and $R^4$, independently of one another, are hydrogen or $(C_1-C_4)$-alkyl, $R^5$ and $R^6$, independently of one another, are hydrogen or $(C_1-C_4)$-alkyl, $R^7$ and $R^8$, independently of one another, are phenyl, o-tolyl, cyclohexyl or butyl, and Y is acetate, cyanide, trifluoroacetate, tetrafluoroborate, propionate, benzoate, chloride, bromide, iodide, fluoride, sulfate, hydrogensulfate, nitrate, phosphate, hexafluorophosphate, tetrafluoroborate, tosylate, mesylate, acetylacetonate, hexafluoroacetylacetonate or pyrazolyl.

16. The process as claimed in claim 6, wherein said palladacycle is selected from the group consisting of:

trans-di-$\mu$-acetato-bis{o-(di-o-tolylphosphino)benzyl}dipalladium(II), trans-di-$\mu$-acetato-bis{o-dimesitylphosphino)-3,5-dimethylbenzyl}dipalladium(II) and di-$\mu$-acetato-bis{o-(cyclohexyl-o-tolylphosphino)benzyl}dipalladium(II).

17. The process as claimed in claim 6, wherein said solvent is toluene or xylene.

18. The process as claimed in claim 6, wherein said solvent is mesitylene, methylnaphthaline, anisole, toluene or xylene.

19. The process as claimed in claim 6, wherein said solvent is mesitylene, methylnaphthaline, anisole, toluene or xylene, and wherein the phosphane of the formula (II) is used in a molar ratio to the palladium compound of the formula (III), (IV) or (V) of from 0.1 to 20.

20. A process for preparing a palladacycle of the formula (I)

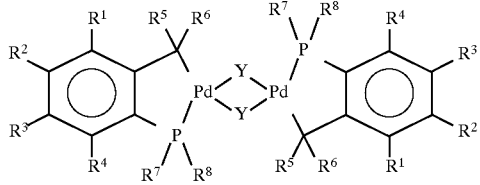

where:
- $R^1$, $R^2$, $R^3$, $R^4$, $R^5$ and $R^6$ are, independently of one another, hydrogen, $(C_1-C_4)$-alkyl, $(C_1-C_4)$-alkoxy, fluorine, $NH_2$, NH-alkyl$(C_1-C_4)$, N(alkyl)$_2$-$(C_1-C_4)$, $CO_2$-$(C_1-C_4)$-alkyl, OCO-alkyl-$(C_1-C_4)$, or phenyl,
- $R^7$ and $R^8$ are, independently of one another, $(C_1-C_8)$-alkyl, $(C_3-C_{12})$-cycloalkyl, substituted or unsubstituted aryl
- or where $R^1$ and $R^2$, $R^2$ and $R^3$, $R^3$ and $R^4$, $R^5$ and $R^6$ together form an aliphatic or aromatic ring, and
- Y is an anion of an inorganic or organic acid, which comprises reacting a phosphane of the formula (II)

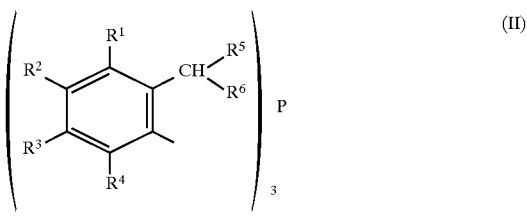

where $R^1$ to $R^6$ are as defined above with a palladium complex of the formula (IV) or an alkali metal palladate of the formula (V)

$$Pd\, Y_2 L_2 \qquad (IV)$$

$$M_2\{PdY_4\} \qquad (V)$$

where Y is as defined above M is sodium, potassium or lithium and L is 1,5-cyclooctadiene in the presence of an organic solvent.

* * * * *